(12) United States Patent
Andersson et al.

(10) Patent No.: US 10,330,489 B1
(45) Date of Patent: Jun. 25, 2019

(54) NAVIGATION USING SENSOR FUSION

(71) Applicant: Google LLC, Mountain View, CA (US)

(72) Inventors: Eve Astrid Andersson, Brooklyn, NY (US); Casey John Burkhardt, Mountain View, CA (US); John Ove Peter Nilsson Lundblad, Milpitas, CA (US); David Tseng, San Jose, CA (US); Charles L. Chen, San Jose, CA (US); Ying Zheng, Mountain View, CA (US); Tiruvilwamalai Venkatram Raman, San Jose, CA (US)

(73) Assignee: Google LLC, Mountain View, CA (US)

( * ) Notice: Subject to any disclaimer, the term of this patent is extended or adjusted under 35 U.S.C. 154(b) by 103 days.

(21) Appl. No.: 15/585,451

(22) Filed: May 3, 2017

Related U.S. Application Data

(63) Continuation of application No. 14/826,425, filed on Aug. 14, 2015, now Pat. No. 9,661,466, which is a
(Continued)

(51) Int. Cl.
*G01C 21/36* (2006.01)
*G01C 21/34* (2006.01)
(Continued)

(52) U.S. Cl.
CPC ......... *G01C 21/3667* (2013.01); *G01C 21/34* (2013.01); *A61B 5/6804* (2013.01);
(Continued)

(58) Field of Classification Search
CPC ....... B60R 1/005; B60R 11/04; A61B 5/6804; A61B 5/02438; A61B 5/02055;
(Continued)

(56) References Cited

U.S. PATENT DOCUMENTS

| 8,989,972 B2 * | 3/2015 | Anderson | A61B 5/6804 |
| | | | 701/301 |
| 2004/0017486 A1 * | 1/2004 | Cooper | H04N 5/073 |
| | | | 348/211.1 |

(Continued)

OTHER PUBLICATIONS

Alzantot et al., "CrowdInside: Automatic Construction of Indoor Floorplans," 20th ACM SIGSPATIAL International Conference on Advances in Geographic Information Systems, Sep. 17, 2012, 11 pages.

(Continued)

*Primary Examiner* — Behrang Badii
(74) *Attorney, Agent, or Firm* — Fish & Richardson P.C.

(57) ABSTRACT

Methods, systems, and apparatus, including computer programs encoded on computer storage media, for resolving erroneous movement signals and for providing navigation instructions. One of the methods includes receiving data from two or more sensors, synchronizing the received data, determining a first subset of the synchronized data from the camera for a particular period of time and a second subset of the synchronized data from the other sensor for the particular period of time, comparing the first subset with the second subset to determine whether the first subset and the second subset indicate an erroneous movement signal, based on determining that the first subset and the second subset indicate an erroneous movement signal, selecting data for one of the sensors based on a sensor priority scheme for the sensors, and resolving the erroneous movement signal based on the selected data for the one of the sensors.

20 Claims, 4 Drawing Sheets

Related U.S. Application Data continuation of application No. 14/212,978, filed on Mar. 14, 2014, now Pat. No. 9,140,555.

(51) Int. Cl.

| | | |
|---|---|---|
| H04N 5/228 | (2006.01) | |
| H04N 5/04 | (2006.01) | |
| H04N 5/222 | (2006.01) | |
| H04N 5/073 | (2006.01) | |
| H04N 5/067 | (2006.01) | |
| H04N 7/18 | (2006.01) | |
| G01C 22/00 | (2006.01) | |
| H04R 5/02 | (2006.01) | |
| A61B 5/00 | (2006.01) | |
| B60R 1/00 | (2006.01) | |
| G05D 1/00 | (2006.01) | |
| B60R 11/04 | (2006.01) | |

(52) U.S. Cl.
CPC ............. *B60R 1/005* (2013.01); *B60R 11/04* (2013.01); *G01C 22/00* (2013.01); *G05D 1/00* (2013.01); *H04N 5/04* (2013.01); *H04N 5/067* (2013.01); *H04N 5/073* (2013.01); *H04N 5/222* (2013.01); *H04N 5/228* (2013.01); *H04N 7/18* (2013.01); *H04R 5/023* (2013.01)

(58) Field of Classification Search
CPC ...... A61B 5/1112; H04N 5/222; H04N 5/073; H04N 5/067; H04N 5/228; H04N 5/04; H04N 7/18; H04N 5/2251; H04N 5/23203; H04N 5/23206; H04N 5/2353; H04N 5/232; H04N 5/235; G05D 1/00; G05D 1/0088; G05D 1/31; G05D 1/024; G05D 1/0274; G05D 1/0033; G01C 22/00; G01C 21/3667; G01C 21/34; G06K 9/209; G06K 9/00818; G08G 1/096716; G08G 1/09675; G08G 1/096783; G08G 1/166; H04R 5/023; B60Q 1/26; B60Q 5/001; G01S 13/867; G01S 13/09; G08C 17/02; H04Q 9/00

See application file for complete search history.

(56) References Cited

U.S. PATENT DOCUMENTS

| | | | | |
|---|---|---|---|---|
| 2011/0176002 | A1* | 7/2011 | Bury | ........................ B60R 1/005 348/148 |
| 2012/0274793 | A1* | 11/2012 | Choi | ........................ H04N 5/222 348/207.11 |
| 2016/0137126 | A1 | 5/2016 | Fursich | |
| 2016/0229342 | A1 | 8/2016 | Taylor | |

OTHER PUBLICATIONS

Saxena et al., "Make3D: Depth Perception from a Single Still Image," Association for the Advancement of Artificial Intelligence, 2008, 1571-1576.
WMS Help, "Introduction," retrieved on Feb. 8, 2014. Retrieved from the internet: URL<http://www.ems-i.com/wmshelp/Introduction/Introduction.htm>, 1 page.
WMS Help, "Map Tools," retrieved on Feb. 8, 2014. Retrieved from the internet: URL<http://www.ems-i.com/wmshelp/General/Tool_Palettes/Map.htm>, 2 pages.
WMS Help, "The Map Module," retrieved on Feb. 8, 2014. Retrieved from the internet: URL<http://www.ems-i.com/wmshelp/Map/Map_Module_Intro.htm>, 1 page.
WMS Help, "Feature Objects," retrieved on Feb. 8, 2014. Retrieved from the internet: URL<http://www.ems-i.com/wmshelp/Map/Feature_Objects/Feature_Objects.htm>, 1 page.
Smit et al., "Real time depth mapping performed on an autonomous stereo vision module," Proceedings ProRISC, Veldhoven, The Netherlands, Nov. 25-26, 2004 306-310.
Litomisky, "Removing Moving Objects from Point Cloud Scenes," Int. Workshop on Depth Image Analysis, 2012, 1-10.
Simonite, "Depth-Sensing Cameras Head to Mobile Devices," MIT Technology Review, Oct. 1, 2013 [retrieved on Feb. 8, 2014]. Retrieved from the internet: URL<http://www.technologyreview.com/news/519546/depth-sensing-cameras-head-to-mobile-devices/>, 2 pages.
Kang et al., "Extracting View-Dependent Depth Maps from a Collection of Images," International Journal of Computer Vision, 58(2):139-163, 2004.
'Wikipedia' [online]. "Interest point detection," Jun. 1, 2013 [retrieved on Feb. 8, 2014. Retrieved from the internet: URL<http://en.wikipedia.org/w/index.php?title=Interest_point_detection&oldid=557814863>, pages.
'Google Maps' [online]. "What is indoor Google Maps?" retrieved on Feb. 7, 2014. Retrieved from the internet: URL<http://maps.google.com/help/maps/indoormaps/>, 4 pages.
Stückler et al., "Interest Point Detection in Depth Images through Scale-Space Surface Analysis," Proceedings of IEEE International Conference on Robotics and Automation (ICRA), Shanghai, China, May 2011, 3568-3574.
Rudinac et al., "Saliency Detection and Object Localization in Indoor Environments," 2010 20th International Conference on Pattern Recognition (ICPR), 404-407. Abstract only [retrieved on Feb. 8, 2014]. Retrieved from the internet: URL<http://ieeexplore.ieee.org/xpl/login.jsp?tp=&arnumber=5597817&url=http>, 2 pages.
TechNewsDaily, "How to become a walking mapmaker," Mother Nature Network, Sep. 25, 2012 [retrieved on Feb. 8, 2014]. Retrieved from the internet: URL<http://www.mnn.com/green-tech/gadgets-electronics/stories/how-to-become-a-walking-mapmaker>, 5 pages.
'Google Mobile' [online]. "Google Maps for Android," retrieved on Feb. 8, 2014. Retrieved from the internet: URL<http://www.google.com/mobile/maps/>, 8 pages.
O'Dell, "Google Maps for Android gets indoor directions. Because walking indoors is hard, y'all," May 9, 2012 [retrieved on Feb. 8, 2014]. Retrieved from the internet: URL<http://venturebeat.com/2012/05/09/google-maps-for-android-gets-indoor-directions-because-walking-indoors-is-hard-yall/, 4 pages.
Gil et al., "A comparative evaluation of interest point detectors and local descriptors for visual SLAM," Machine Vision and Applications (2010), 21:905-920.
'Don Dodge' [online]. "Why Indoor Location will be bigger than GPS or Maps, and how it works," Don Dodge on the Next Big Thing, Apr. 2, 2013 [retrieved on Feb. 8, 2014]. Retrieved from the internet: URL<http://dondodge.typepad.com/the_next_big_thing/2013/04/why-indoor-location-will-be-bigger-than-gps-or-maps.html>, 3 pages.
Krumm et al., "Multi-Camera Multi-Person Tracking for EasyLiving," Third IEEE International Workshop on Visual Surveillance, Jul. 1, 2000, Dublin, Ireland, 1-8.
Saxena et al., "Depth Estimation using Monocular and Stereo Cues," IJCAI, 2007, 2197-2203.
Coughlan et al., "Terrain Analysis for Blind Wheelchair Users: Computer Vision Algorithms for Finding Curbs and Other Negative Obstacles," Conference & Workshop on Assistive Technologies for People with Vision & Hearing Impairments (CVHI), 2007, 1-6.
'ArcGIS' [online]. "ArcGIS Help 10.1—Exercise 1a: Creating new points," Sep. 30, 2013 [retrieved on Feb. 8, 2014]. Retrieved from the internet: URL<http://resources.arcgis.com/en/help/main/10.1/index.html#//01m600000>, 1 page.

* cited by examiner

NAVIGATION USING SENSOR FUSION

CROSS-REFERENCE TO RELATED APPLICATION

This application is a continuation of U.S. application Ser. No. 14/826,425, filed Aug. 14, 2015, which is a continuation of U.S. application Ser. No. 14/212,978, filed Mar. 14, 2014, the contents of which are herein incorporated by reference.

BACKGROUND

This specification relates to creating maps and providing navigation instructions using a mobile device.

A user may access a map to receive directions to get from a current physical location to another location. The map may be a hardcopy, e.g., paper copy, or an electronic map. While there are many maps available for outdoor environments, maps are lacking for indoor environments. Furthermore, what indoor maps do exist are often insufficient for guided indoor navigation.

SUMMARY

In general, one innovative aspect of the subject matter described in this specification can be embodied in methods that include the actions of receiving, at a user device, data from two or more sensors included in the user device, the two or more sensors including a camera and another sensor, synchronizing the received data from the two or more sensors so that the data from the camera corresponds in time to the data from the other sensor, determining a first subset of the synchronized data from the camera for a particular period of time and a second subset of the synchronized data from the other sensor for the particular period of time, the first subset of the synchronized data and the second subset of the synchronized data each being representative of movement of the user device and the first subset of the synchronized data being representative of objects in a physical area surrounding a particular physical location of the user device, comparing the first subset of the synchronized data with the second subset of the synchronized data to determine whether the first subset and the second subset indicate an erroneous movement signal, based on determining that the first subset and the second subset indicate an erroneous movement signal, selecting, from the first subset and the second subset of the synchronized data, data for one of the sensors, the selection based on a sensor priority scheme for the sensors, and resolving the erroneous movement signal based on the selected data for the one of the sensors. Other embodiments of this aspect include corresponding computer systems, apparatus, and computer programs recorded on one or more computer storage devices, each configured to perform the actions of the methods. A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

The foregoing and other embodiments can each optionally include one or more of the following features, alone or in combination. In particular, one embodiment may include all the following features in combination. The first subset of the synchronized data may represent at least two image frames. The sensor priority scheme may indicate that the other sensor has a higher priority than the camera. The selected data for one of the sensors may indicate that the user device is not moving. The method may include discarding the first subset and the second subset of the synchronized data.

In some implementations, the selected data for one of the sensors indicate that the user device is moving. The method may include determining a plurality of feature points of the physical area using at least the first subset of the synchronized data, and providing navigation instructions to a user using the plurality of feature points. Providing the navigation instructions to the user using the plurality of feature points may include providing at least one navigation instruction selected from the group consisting of an audible instruction, a haptic instruction, and a visual instruction. The audible instruction may include an audible tone or verbal instruction.

In some implementations, the method includes determining whether the plurality of feature points indicate that the particular physical location of the user device corresponds with a particular location on a map, wherein providing the navigation instructions to the user using the plurality of feature points includes providing the navigation instructions based on the particular location on the map. The method may include receiving, by the user device, identification of a particular destination on the map, wherein providing the navigation instructions based on the particular location on the map includes providing the navigation instructions based on the particular location on the map and the particular destination on the map. The method may include determining a probability that the particular physical location of the user device corresponds with the particular location on the map. The method may include detecting, using the feature points, an object not represented in the map, wherein providing the navigation instructions to the user includes providing navigation instructions based on a physical location of the object. The method may include creating a map using the feature points. The method may include determining, using at least the first subset of the synchronized data, that at least one of the feature points represents a moving object, and not using the at least one of the feature points that represents the moving object when creating the map. The method may include sending the map to a server to allow other user devices to use the map to provide navigation instructions for the physical area represented in the map.

In some implementations, the particular physical location of the user device includes a physical indoor location. The two or more sensors may include at least one sensor selected from the group consisting of an accelerometer, a gyroscope, a global positioning system receiver, and a wireless receiver.

The subject matter described in this specification can be implemented in particular embodiments so as to realize one or more of the following advantages. In some implementations, a user device may use movement data from multiple sensors to verify the accuracy of the movement data. In some implementations, a priority scheme, e.g., that ranks the sensors, may be used to determine which movement data is accurate. In some implementations, a user device may provide navigation instructions to a user, e.g., a visually impaired user, to guide the user around objects that may not remain in the same physical location or which are difficult to detect, e.g., using a cane or guide dog. In some implementations, the use of movement data from multiple sensors may provide high accuracy navigation instructions, e.g., within centimeter level accuracy. In some implementations, a user device may determine accurate navigation instructions without receiving signals from wireless access points or wireless beacons in the physical environment.

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION 1.0 Overview

Sometimes a user may want to navigate an area with which they are unfamiliar, such as a mall or an office building that the user has not previously visited. The user may launch a map application, on a user device, that includes a map of the building and provides detailed navigation instructions to guide the user to the user's intended destination. In some implementations, the map application also provides assistive features to help guide visually impaired users to their intended destination. For example, the map application may provide tactile or audible feedback that informs a visually impaired user of his or her current location, directions, and potential obstacles.

The map application receives input from multiple sensors included in the user device, including a camera and another sensor such as an accelerometer or a gyroscope, and synchronizes the data received from the different sensors so that the data corresponds in time. For instance, the map application synchronizes the data so that data recorded by the accelerometer at a particular instant in time corresponds with data recorded by the camera at the same instant in time.

The map application may use the synchronized data to determine whether the user device, and the user carrying the user device, is moving, the direction in which the user device is moving, or if the user device is substantially stationary, e.g., when the user is not walking and not moving the user device. The map application may also use the synchronized data to determine a type of movement of the user device, e.g., if the user is moving the user device vertically while standing still or the user is walking while carrying the user device.

The map application may detect feature points in images received from the camera, correlate the feature points with feature points represented in a map of the building, e.g., where the feature points represent objects in the map and match data associated with those objects, and determine a physical location of the user device (and thus, by extension, the physical location of the user carrying or wearing the user device). The map application may use the determined physical location of the user device and the desired destination of the user to provide instructions to the user.

When the map application determines that some sensors indicate that the user device is moving and other sensors indicate that the user device is not moving, the map application may determine a priority of the sensors and use the movement data from the highest priority sensor to determine whether the user device is moving or not. For example, when the sensors include a camera and an accelerometer, the accelerometer may have a higher priority than the camera.

1.1 Example Operating Environment

Figure 1:
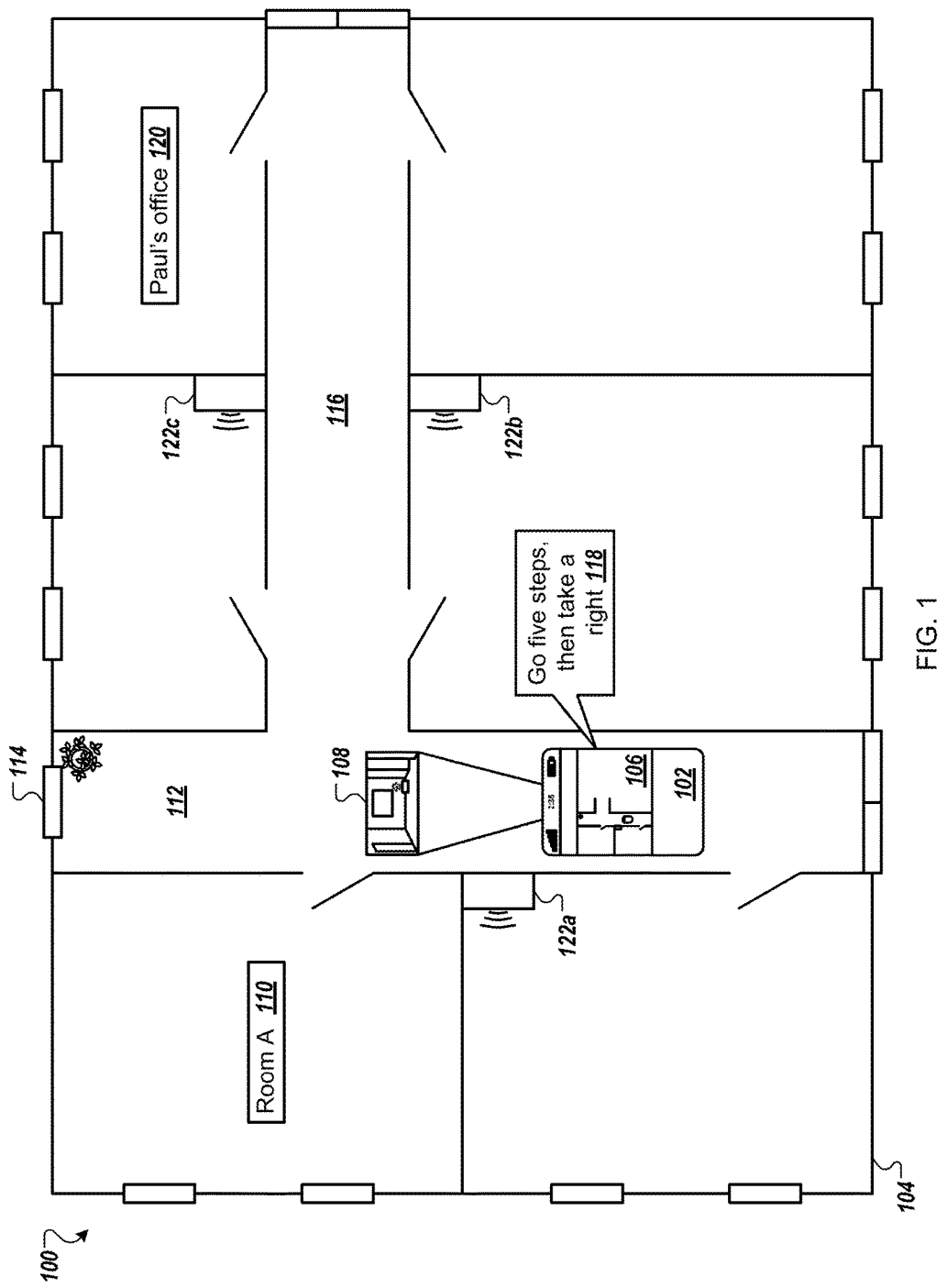
FIG. 1 is an example of an environment with a user device navigating a building.

FIG. 1 is an example of an environment 100 with a user device 102 navigating a building 104. The user device 102 includes multiple sensors such as a camera, an accelerometer, and at least one wireless receiver. More details of the user device 102 are described below with reference to FIG. 2.

As the user device 102 moves, the user device 102 receives data from the multiple sensors and creates a map 106 of the building 104. The user device 102 can use some of the data, such as an image frame 108 or other depth data, to identify feature points that represent objects in the building. For instance, the objects may include a door, a window, a hallway, and a plant. A variety of image processing techniques may be used to extract feature data from captured images, such as Canny detection, phase congruency edge detection, and the like. Other features can also be detected, such as corner features and blob features. Any appropriate feature detection image processing algorithms can be used to detect such features.

The user device 102 may use the feature points to provide navigation instructions to a user operating the user device 102. For example, the user device 102 may be able to determine that a room A 110 to the left of the user is not the user's intended destination based on a room name identified in the image frame 108, e.g., when the room name is on a sign outside the room A 110. The user device 102 may determine that a hallway 112 in which the user is walking ends, upon detection of a window 114, and that the user should take a right when the user device 102 reaches a particular position that corresponds with another crossing hallway 116, e.g., after the user takes five steps. Such determinations can be based on, for example, comparison of detected features to a comparison of pre-mapped feature data. The pre-mapped feature data may be provided to the user device by a third party, such as in the case of a building that provides such map data to user devices, or may have been previously generated and stored by use of the user device.

The user device 102 may provide audible, haptic, and/or visual navigation instructions to the user. For instance, the user device 102 may present the map 106 on a display showing the current location of the user device and features of the building 104, such as the room 110, the hallway 112, and the window 114. The user device 102 may also provide audible instructions "Go five steps, then take a right" 118.

In some examples, the user device 102 may assist the user in finding the user's intended destination when the user device 102 does not already have a map for the building 104 or, if the user device 102 has a map for the building, when the user does not know the exact location of the destination, e.g., but knows that they would like to find Paul's office 120.

The user device 102 may create the map as the user moves through the building 104, as shown in FIG. 1. However, as described above and discussed in more detail below, the user device 102 can also receive a map of the building 104 from a server.

The user device 102 may also receive signatures, e.g., media access control addresses, from one or more wireless access points or beacons 122a-c, such as a Wi-Fi access point or a Bluetooth beacon. The user device 102 may use the signatures from the wireless access points 122a-c to determine a wireless fingerprint for the current physical location of the user device 102. When creating a map, the user device 102 may associate the wireless fingerprint with a position on the map 106 corresponding with the current physical location of the user device 102.

When the user device 102 uses a previously generated map for the building 104, the user device 102 may determine a wireless fingerprint using the strength and particular combination of signals from the wireless access points 122a-c and identify a location on the map 106, which corresponds with the physical location of the user device 102, using the determined wireless fingerprint.

The user device 102 may determine a particular physical location of the user device 102 in the building 104 using the wireless fingerprint, the feature points identified in the image frame 108, and data from other sensors, such as an accelerometer and/or a gyroscope. For example, the data from the various sensors may not agree about the particular physical location of the user device 102 in the building and the user device 102 may apply different weights to the separate data, e.g., according to a location priority scheme, to determine the particular physical location. In some implementations, the feature points from the image frame 108 may have a greater weight than data received from the wireless access points 122a-c and data from an accelerometer or a gyroscope. In some examples, the user device 102 may use only the feature points from the image frame 108 to determine the particular physical location.

In some examples, the user device 102 may receive erroneous movement data from the various sensors that indicates that the user device 102 is both moving and remaining in the same position. For instance, the user device 102 may receive a sequence of image frames that contain moving objects, and determine that the user device 102 is moving based on the moving objects in the image frames. The user device 102 may also receive data from an accelerometer for the same period of time that indicates that the user device 102 is not moving.

The user device 102 may use a movement priority scheme to determine whether or not the user device 102 is moving. For instance, the movement priority scheme may indicate that the accelerometer has a higher priority and, using the data from the accelerometer, the user device 102 may determine that the user device 102 is not moving. This priority scheme is useful when the accelerometer data may more reliably indicate a user is stationary; for example, a user may be moving his or her user device in a swinging motion, and from the readings of the accelerometer it may be clear that the user device is oscillating about particular point, while analysis of image features may be ambiguous as to movement. Conversely, if the camera has a higher priority than the accelerometer, the user device 102 would use the data from the sequence of image frames and determine that the user device 102 is moving.

In some implementations, the movement priority scheme may include multiple different priority schemes based on the types of data received from the sensors included in the user device 102. For instance, when all of the sensors indicate that the user device 102 is moving but the data disagree about the movement speed of the user device 102, the user device may rely upon the images frames received from a camera to determine an actual movement speed of the user device 102. In some examples, when an accelerometer indicates that the movement of the user device 102 is very slow, the user device 102 may determine that the user device is remaining in substantially the same physical location in the building 104. For example, the user operating the user device 102 may be standing still while moving the user device 102, e.g., up, down, and/or side to side. In some examples, the user device 102 may determine that the user device 102 is in substantially the same physical location and not create new feature points for the map 106 or provide navigation instructions to the user until the user begins to move again.

In some examples, when a gyroscope indicates that the user device 102 is rotating and the camera indicates that the client is moving, e.g., based on changes in a sequence of image frames as the user device 102 turns, the user device 102 may determine that the user device 102 is remaining in substantially the same physical location of the building 104.

1.2 Example System

Figure 2:
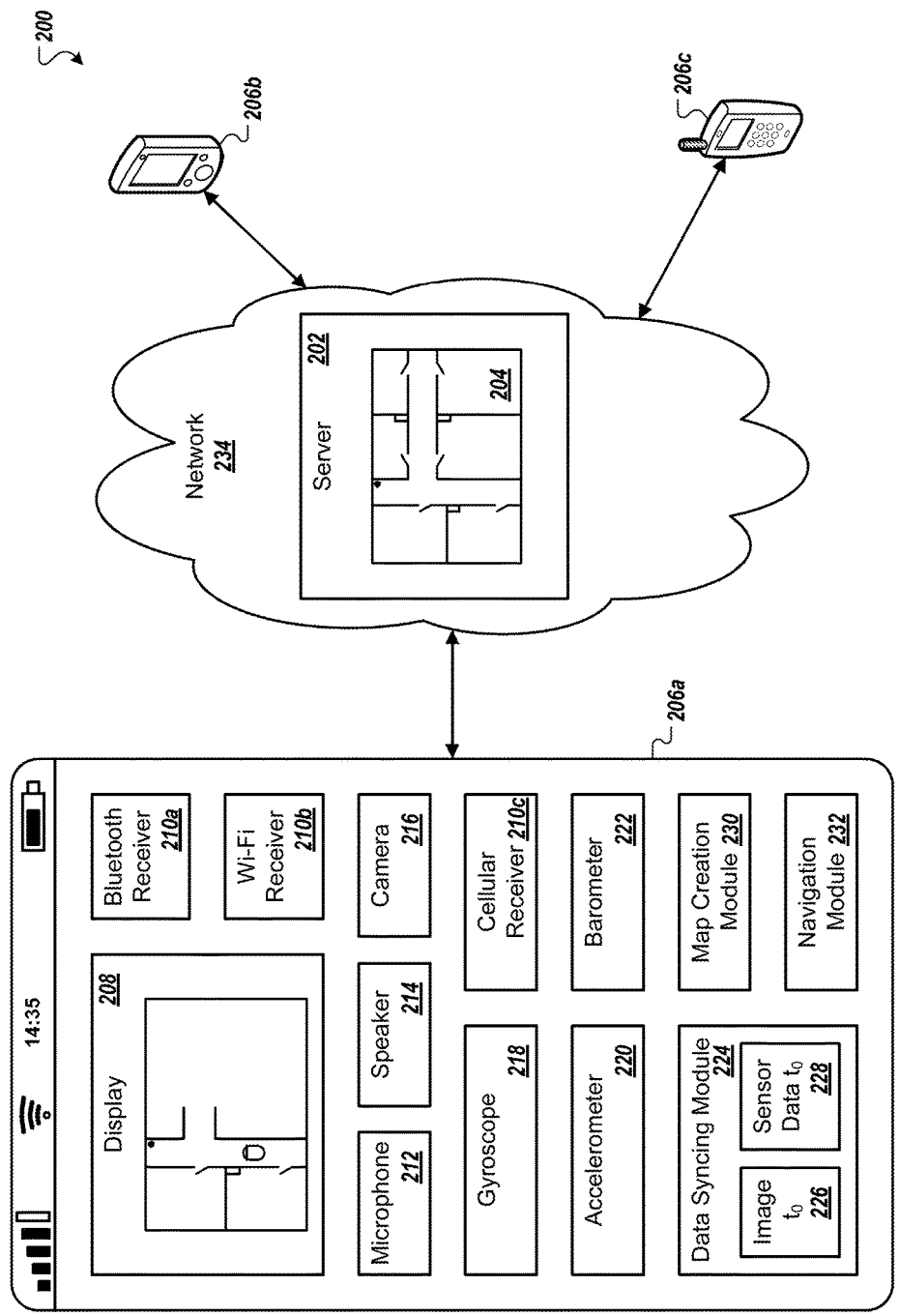
FIG. 2 is an example of a system for sending and receiving map data.

FIG. 2 is an example of a system 200 for sending and receiving map data. The system 200 includes a server 202 with a database of maps 204. The server 202 may receive a message from a user device 206a-c requesting one of the maps 204, e.g., which corresponds with a physical location surrounding the requesting user device 206a-c or a physical location to which the requesting user device 206a-c may visit.

In some examples, one of the user devices 206a-c may create a map or update a map, e.g., based on movement or addition of an object to the physical area represented by the map. For instance, the user device 206a may determine that a location of a desk in an office was moved or a couch was added to a room and may send data to the server 202 identifying the object, e.g., feature points that represent the object, and the physical location of the object. The server may use the received data to update the corresponding map 204 accordingly and send the updated version of the map in response to a future request for the map.

The user device 206a includes a display 208 that provides a user with visual feedback. The display 208 may present an image of a map received from the server 202 or an image of a map that is currently being generated by the user device 206a.

The user device 206a includes multiple wireless receivers 210a-c. The wireless receivers 210a-c may include a Bluetooth receiver 210a, a Wi-Fi receiver 210b, a cellular receiver 210c, and a global positioning system (GPS) receiver. The user device 206a may use the wireless receivers 210a-c to determine a wireless fingerprint received at a particular time by the user device 206a. The wireless fingerprint may be associated with a specific location on a map when the user device 206a creates a map. The user device 206a may use a wireless fingerprint to identify a specific location on a previously created map, e.g., upon determining that data representing that the wireless fingerprint is typically received when the physical location of the user device 206 corresponds with the specific location on the map. The user device 206a may use the specific location to determine a physical location of the user device 206a, alone or with other data representing a physical location of the user device 206a, e.g., by combining multiple estimated physical location determinations.

The user device 206a includes a microphone 212 that can receive audible commands from a user operating the user device 206a and a speaker 214 that can provide audible notifications to the user.

A camera 216, included in the user device 206a, may provide the user device 206a with an image or a sequence of images, e.g., a video stream. The user device 206a may use the images to generate and/or navigate a map. The camera 216 may be a standard camera and/or may provide the user device 206a with depth data. For instance, the camera 216 may provide the user device 206a with stereo images.

The user device 206a may include a gyroscope 218, an accelerometer 220, and/or a barometer 222 and use signals from these sensors to determine whether and how much the user device 206a has moved.

The user device 206a may send data from the sensors to a data syncing module 224 that synchronizes the data from the different sensors. For instance, an image 226 taken at t0 may be received by the data syncing module 224 after the data syncing module 224 receives sensor data 228 that was also recorded at t0.

The data syncing module 224 aligns the data from the different sources and provides the synced data to a map creation module 230 and/or a navigation module 232 so that the respective modules may analyze the data for a particular time or period of time. For example, the map creation module 230 may compare the image frame data from t0 and ti with the accelerometer data from t0 and ti to determine whether the two sensors have erroneous movement signals, e.g., where one set of data indicates that the user device 206a is moving while the other set of data indicates that the user device 206a is not moving.

The map creation module 230 may use the synced data to create or update a map of a physical area in which the user device 206a is located. For instance, when the user device 206a receives a map from the server 202, the map creation module 230 may update the map upon determining that an object represented in the map, e.g., a desk or chair, has moved or that an object has been added to the physical area, e.g., a plant or a table.

The navigation module 232 uses the synced data to provide the user operating the user device 206a with navigation instructions. The navigation module 232 may determine a location on a map which corresponds with the physical location of the user device 206a and provide the navigation instructions based on the location on the map.

The navigation module 232 may coordinate with the map creation module 230 when determining the location on the map. For instance, the map creation module 230 may determine the location on the map, update the map upon determining that an object in the physical area has moved, and provide data representing the location on the map to the navigation module 232.

One or more of the sensors included in the user device 206a may provide the user device 206a with depth information. For example, the camera 216 may provide the user device 206a with depth information along with the image frames. The camera may be an infrared projection camera, a time of flight camera, a stereo camera, or any other appropriate type of camera with depth information. In some examples, the user device 206a may include a range finder, e.g., a laser range finder or sonar.

A user device may send a map to a server to allow other user devices to use the map to provide navigation instructions for a physical area represented in the map. For instance, the user device B 206b may create a map and send the map to a server. The user device C 206c may request the map and use the map to provide navigation instructions to a user operating the user device C 206c.

The user devices 206a-c may include personal computers, mobile communication devices, and other devices that can send and receive data over a network 234. The network 234, such as a local area network (LAN), wide area network (WAN), the Internet, or a combination thereof, connects the user devices 206a-c and the server 202.

2.0 Example Process Flow

Figure 3:
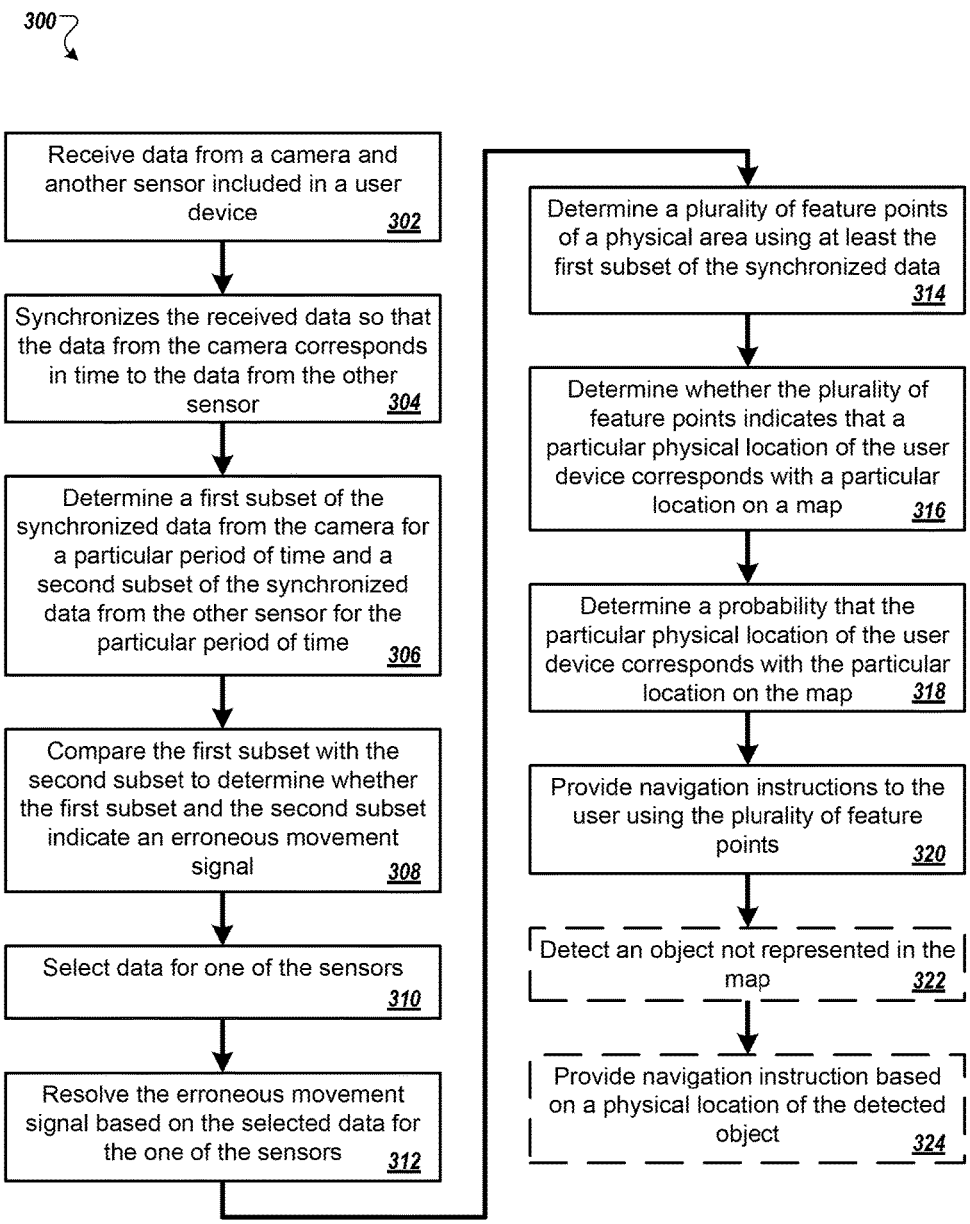
FIG. 3 is a flow diagram of a process for providing navigation instructions.

FIG. 3 is a flow diagram of a process 300 for providing navigation instructions. For example, the process 300 can be used by the user device 102 from the environment 100.

The process 300 receives data from a camera and another sensor included in a user device (302). The user device includes two or more sensors including the camera and the other sensor. The other sensor may be an accelerometer, a gyroscope, or a wireless receiver to name a few examples.

The process 300 synchronizes the received data so that the data from the camera corresponds in time to the data from the other sensor (304). The user device may use any appropriate algorithm to synchronize the data received from the various sensors included in the user device. For example, each sensor can tag its corresponding data with a timestamp from a system clock for time alignment. In some examples, the data from the separate sensors is received by a single chip or buffer that syncs the sensor data in time. Other synchronization algorithms can also be used.

The user device may use the synchronized data to determine the movement of the user device. For example, the user device may use the data for a particular period of time, e.g., multiple image frames and data from the other sensors for the same period of time as the image frames, to compensate for the movement, e.g., gait, of the user carrying the user device when creating a map and/or determining the particular physical location of the user device.

The process 300 determines a first subset of the synchronized data from the camera for a particular period of time and a second subset of the synchronized data from the other sensor for the particular period of time (306). The first subset of the synchronized data and the second subset of the synchronized data each are representative of movement of the user device. In the case of a user device with a camera and an accelerometer, the first subset of the synchronized data is image feature data that is representative of objects in a physical area surrounding a particular physical location of the user device, and the second subset of data is accelerometer data. Because both subsets of data can be processed to determine movement, both subsets are representative of movement of the user device. In general, both subsets of data can be processed for movement detection, and at least one subset of data is also representative of objects.

The first subset of the synchronized data may represent at least two image frames. The image frames may be separate still images frames taken by the camera at different times or may be still image frames extracted from a continuous sequence of images frames taken by the camera, e.g., as part of a video.

The process 300 compares the first subset with the second subset to determine whether the first subset and the second subset indicate an erroneous movement signal (308). For example, the user device determines whether the first subset indicates that the user device is moving and, separately, whether the second subset indicates that the user device is moving.

In response to determining that the first subset and the second subset indicate an erroneous movement signal, the process 300 selects data for one of the sensors (310). The user device may select the data based on a sensor priority scheme for the sensors. For example, the other sensor, e.g., an accelerometer or a gyroscope, may have a higher priority than the camera. The sensor priority scheme may include different priorities for one or more of the sensors based on the types of input received from the sensors. For example, if an accelerometer indicates that the user device is moving at a first speed, the accelerometer may have a first priority, if the accelerometer indicates that the user device is moving at a second, slower speed, the accelerometer may have a second priority, and if the accelerometer indicates that the user device is not moving, the accelerometer may have a third priority, e.g., higher than the first and second priorities.

The process 300 resolves the erroneous movement signal based on the selected data for the one of the sensors (312). For example, the user device uses the data from the accelerometer to determine whether or not the user device is moving.

When the selected data for one of the sensors indicate that the user device is not moving, the user device may restart the process 300 or end execution of the process 300. In some examples, the user device may discard the first subset and the second subset of the synchronized data upon determining that the user device is not moving.

When the selected data for one of the sensors indicate that the user device is moving, the process 300 may determine a plurality of feature points of a physical area using at least the first subset of the synchronized data (314). For example, the user device may analyze the first subset, e.g., the image frames received from the camera, to determine feature points that represent objects in the physical area surrounding a particular physical location of the user device. If feature analysis was used to determine movement, this step can be skipped, as it was already performed.

The process 300 determines whether the plurality of feature points indicates that the particular physical location of the user device corresponds with a particular location on a map (316). For example, the user device compares the determined feature points with feature points associated with the map to determine the particular location on the map.

In some implementations, the determined feature points may include features identified by the other sensor or additional sensors included in the user device. For instance, the user device may identify a wireless fingerprint using data received by wireless receivers or range data received from a range finder and use the wireless fingerprint and/or the range data to determine the particular location on the map with which the particular physical location of the user device corresponds.

The process 300 determines a probability that the particular physical location of the user device corresponds with the particular location on the map (318). The user device may compare the feature points and data from all the other sensors included in the user device with data representing the particular location on the map to determine any differences between the data and the probability that the user device corresponds with the particular location on the map.

The user device may repeat steps 316 and/or 318 multiple times for different map locations and select the map location with the highest probability as the particular location on the map which corresponds with the particular physical location of the user device.

The process 300 provides navigation instructions to the user using the plurality of feature points (320). For example, the user device may provide an audible instruction, e.g., an audible tone or a verbal instruction, a haptic instruction, and/or a visual instruction. The navigation instructions may be based on the particular location on the map, e.g., indicating the physical location of the user device.

For instance, the instructions indicate that the user should move in a particular direction to avoid an object identified in the map or identified by the sensors included in the user device. The object may be fixed in the area around the user device, may have been moved since the creation of the map, or may have been added to the area around the user device since the map was created.

In some implementations, the user device may receive an identification of a particular destination on the map and provide instructions based on the particular location on the map, e.g., corresponding with the physical location of the user device, and the particular destination on the map. For example, the user device may provide instructions for the user to get from their current location, represented as the particular location on the map, to the particular destination.

Because map data provided to the user device may not be recent, there may be objects not accounted for. For example, a cart may have been left in a hallway, or a box may be left outside a worker's cubicle. The process 300 thus also checks for unmapped objects, and performs additional steps when such objections are detected.

The process 300 detects an object not represented in the map (322). The camera, or another sensor in the user device, may identify the object and the user device may provide navigation instructions to the user to help the user avoid the object, e.g., when the user may be visually impaired. The user device may provide an indication of the object to a server, e.g., which provided the map to the user device. The server may update a network copy of the map with the received information, e.g., the location of the object and other features of the object.

The process 300 provides navigation instructions based on the physical location of the detected object (324). For instance, the user device may instruct the user to walk around the detected object, e.g., a plant, move below the detected object, e.g., a hanging display that requires the user to stoop to avoid contacting the object, or move over the detected object, e.g., a cord.

The order of steps in the process 300 described above is illustrative only, and the providing of the navigation instructions can be performed in different orders. For example, the user device may determine the plurality of feature points prior to comparing the first subset with the second subset.

In some implementations, the process 300 can include additional steps, fewer steps, or some of the steps can be divided into multiple steps. For example, the user device may receive the map from a server. In some implementations, the user device creates the map using the feature points. The user device may send the map to the server upon completion of the map or upon receiving an indication from the user instructing the user device to send the map to the server.

3.0 Optional Implementation Details

In some implementations, the user device determines that at least one of the feature points represents a moving object and does not use the at least one of the feature points that represents the moving object when creating the map. The user device may use the feature points that represent the moving object when providing navigation instructions to the user, e.g., to prevent the user from running into the moving object.

In some implementations, the user device may determine subsets of the synchronized data when each subset of the synchronized data corresponds to a particular physical location of the user device and is representative of objects in a physical area surrounding the particular physical location of the user device and movement of the user device relative to the physical location. The user device may compare at least two of the subsets to determine whether the subsets indicate an erroneous movement signal and select, from the at least two subsets of data, data for one of the sensors. The selection may be based on a sensor priority scheme. The user device may resolve the erroneous movement signal based on the selected data for the one of the sensors.

In some implementations, the user device may send data to the server for processing. For example, the user device may send sensor data to the server, receive navigation data from the server, and provide a user operating the user device with navigation instructions using the navigation data. The server may receive the sensor data, synchronize the sensor data, determine whether the user device is moving, identify the physical location of the user device, and provide navigation data to the user device.

A user device may identify wireless fingerprints alone or in conjunction with a server. The user device may send wireless fingerprint data to a server. The server may determine a physical location of the user device that corresponds with the wireless fingerprint and provide data representing the physical location to the user device.

In some examples, the user device may use GPS data to identify a specific physical area in which the user device is physically located, e.g., a building near the user device. The user device may send wireless fingerprint data to a server to determine a specific building in which the user device is physically located. The user device may use data representing the specific physical area and/or the specific building to request a map, e.g., of the specific building, from the server. The user device may receive wireless fingerprint signature data with the map, store the received wireless fingerprint signature data in memory, and use the local wireless fingerprint signature data to determine a physical location of the user device when the user device is in the specific building, e.g., using wireless fingerprints received from wireless access points or beacons. The user device may use wireless fingerprint data, and/or data from beacons located in a physical environment surrounding the user device, to determine a physical location of the user device more quickly than without the use of the wireless fingerprint data or the beacon data.

4.0 Additional Implementation Details

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non-transitory program carrier for execution by, or to control the operation of, data processing apparatus. Alternatively or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus. The computer storage medium can be a machine-readable storage device, a machine-readable storage substrate, a random or serial access memory device, or a combination of one or more of them.

The term "data processing apparatus" refers to data processing hardware and encompasses all kinds of apparatus, devices, and machines for processing data, including by way of example a programmable processor, a computer, or multiple processors or computers. The apparatus can also be or further include special purpose logic circuitry, e.g., an FPGA (field programmable gate array) or an ASIC (application-specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, a module, a software module, a script, or code, can be written in any form of programming language, including compiled or interpreted languages, or declarative or procedural languages, and it can be deployed in any form, including as a stand-alone program or as a module, component, subroutine, or other unit suitable for use in a computing environment. A computer program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a communication network.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application-specific integrated circuit).

Computers suitable for the execution of a computer program include, by way of example, general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the user device, which acts as a client. Data generated at the user device, e.g., a result of the user interaction, can be received from the user device at the server.

Figure 4:
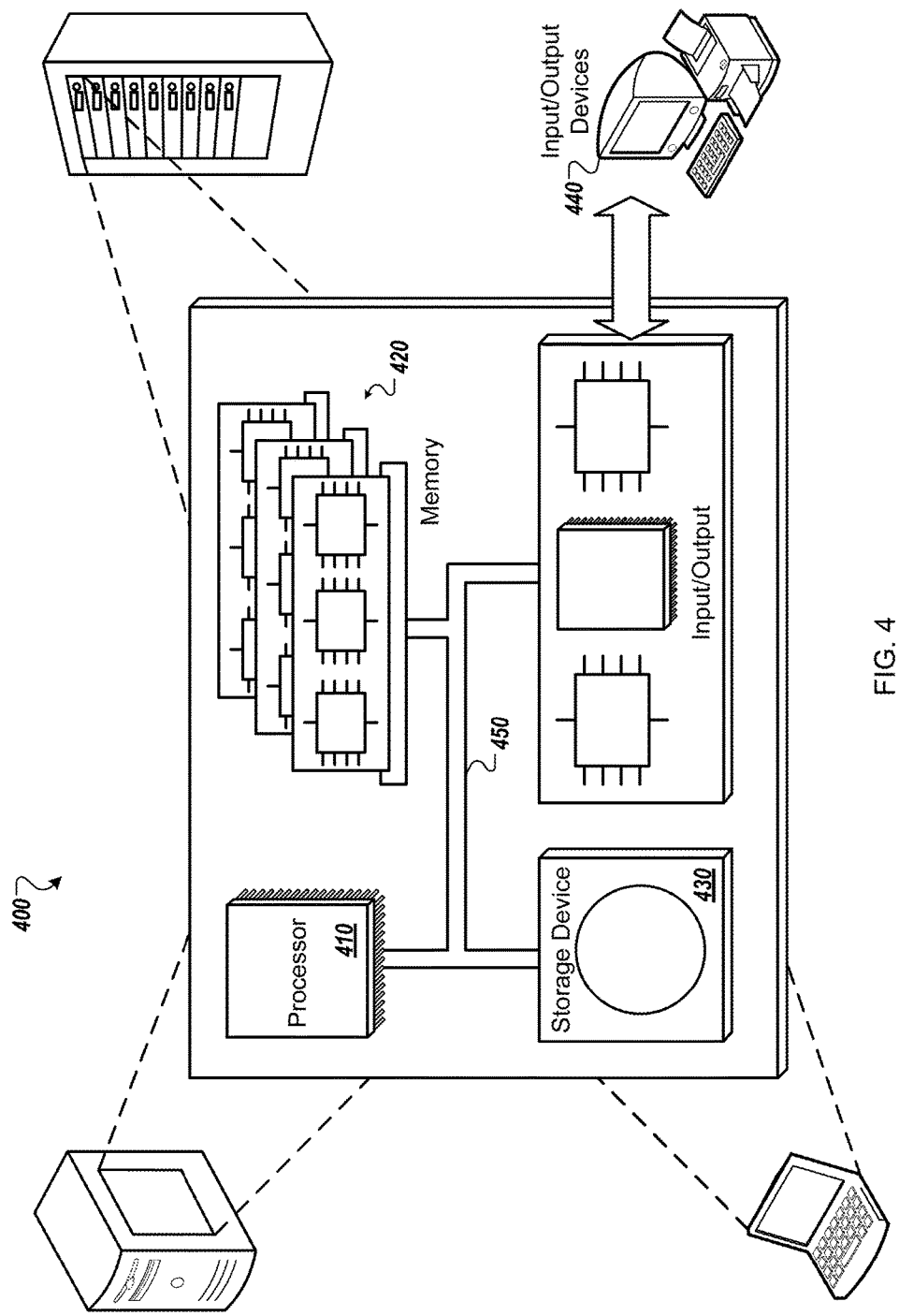
FIG. 4 is a block diagram of a computing system that can be used in connection with computer-implemented methods described in this document.

An example of one such type of computer is shown in FIG. 4, which shows a schematic diagram of a generic computer system 400. The system 400 can be used for the operations described in association with any of the computer-implement methods described previously, according to one implementation. The system 400 includes a processor 410, a memory 420, a storage device 430, and an input/output device 440. Each of the components 410, 420, 430, and 440 are interconnected using a system bus 450. The processor 410 is capable of processing instructions for execution within the system 400. In one implementation, the processor 410 is a single-threaded processor. In another implementation, the processor 410 is a multi-threaded processor. The processor 410 is capable of processing instructions stored in the memory 420 or on the storage device 430 to display graphical information for a user interface on the input/output device 440.

The memory 420 stores information within the system 400. In one implementation, the memory 420 is a computer-readable medium. In one implementation, the memory 420 is a volatile memory unit. In another implementation, the memory 420 is a non-volatile memory unit.

The storage device 430 is capable of providing mass storage for the system 400. In one implementation, the storage device 430 is a computer-readable medium. In various different implementations, the storage device 430 may be a floppy disk device, a hard disk device, an optical disk device, or a tape device.

The input/output device 440 provides input/output operations for the system 400. In one implementation, the input/output device 440 includes a keyboard and/or pointing device. In another implementation, the input/output device 440 includes a display unit for displaying graphical user interfaces.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

What is claimed is:

1. An apparatus, comprising:
two or more sensors comprising a camera and another sensor;
a data processing apparatus; and
a non-transitory computer readable storage medium in data communication with the data processing apparatus and storing instructions executable by the data processing apparatus and upon such execution cause the data processing apparatus to perform operations comprising:
receiving data from the two or more sensors;
synchronizing the received data from the two or more sensors so that the data from the camera corresponds in time to the data from the other sensor;
determining a first subset of the synchronized data from the camera for a period of time and a second subset of the synchronized data from the other sensor for the period of time, the first subset of the synchronized data and the second subset of the synchronized data each being representative of movement of the apparatus and the first subset of the synchronized data being representative of objects in a physical area surrounding a physical location of the apparatus;

determining a plurality of feature points of the physical area using at least the first subset of the synchronized data and the second subset of the synchronized data;

determining, using at least the first subset of the synchronized data, that at least one of the plurality of feature points represents a moving object; and creating a map using one or more of the plurality of feature points, the one or more of the plurality of feature points not including the at least one of the plurality of feature points that represents the moving object.

2. The apparatus of claim 1, wherein determining the plurality of feature points of the physical area using at least the first subset of the synchronized data and the second subset of the synchronized data comprises:

comparing the first subset of the synchronized data with the second subset of the synchronized data to determine whether the first subset of the synchronized data and the second subset indicate an erroneous movement signal; and based on determining that the first subset of the synchronized data and the second subset indicate an erroneous movement signal, detecting the plurality of feature points in one or more images captured by the camera and represented by the first subset of the synchronized data.

3. The apparatus of claim 2, wherein detecting the plurality of feature points in the one or more images captured by the camera and represented by the first subset of the synchronized data comprises detecting the plurality of feature points in two or more images captured by the camera and represented by the first subset of the synchronized data.

4. The apparatus of claim 2, wherein detecting the plurality of feature points in one or more images captured by the camera and represented by the first subset of the synchronized data comprises:

determining a sensor priority scheme for the two or more sensors;

determining, using the sensor priority scheme, that the camera has a higher priority than the other sensor; and selecting the first subset of the synchronized data in response to determining that the camera has a higher priority than the other sensor.

5. The apparatus of claim 1, the operations comprising:

receiving second data from the two or more sensors;

synchronizing the received second data from the two or more sensors so that the second data from the camera corresponds in time to the second data from a third sensor;

determining a third subset of the synchronized second data from the camera for a second period of time and a fourth subset of the synchronized second data from the third sensor for the second period of time;

comparing the third subset of the synchronized second data with the fourth subset of the synchronized second data to determine whether the third subset and the fourth subset indicate an erroneous movement signal;

based on determining that the third subset and the fourth subset indicate an erroneous movement signal, selecting, from the third subset and the fourth subset of the synchronized second data, third data for one of the sensors, the selection based on a sensor priority scheme for the sensors;

determining that the selected third data for one of the sensors indicate that the apparatus is not moving; and discarding the third subset and the fourth subset of the synchronized second data in response to determining that the selected third data for one of the sensors indicate that the apparatus is not moving.

6. The apparatus of claim 5, wherein discarding the first subset and the second subset of the synchronized second data comprises determining not to update the map using the third subset and the fourth subset of the synchronized second data.

7. The apparatus of claim 1, the operations comprising determining navigation instructions using one or more of the plurality of feature points.

8. The apparatus of claim 7, wherein determining the navigation instructions using one or more of the plurality of feature points comprises determining the navigation instructions using one or more of the at least one of the plurality of feature points that represents the moving object.

9. A computer-implemented method comprising:

receiving, at a computer, data from two or more sensors included in the computer, the two or more sensors including a camera and another sensor;

synchronizing the received data from the two or more sensors so that the data from the camera corresponds in time to the data from the other sensor;

determining a first subset of the synchronized data from the camera for a period of time and a second subset of the synchronized data from the other sensor for the period of time, the first subset of the synchronized data and the second subset of the synchronized data each being representative of movement of the computer and the first subset of the synchronized data being representative of objects in a physical area surrounding a physical location of the computer;

determining a plurality of feature points of the physical area using at least the first subset of the synchronized data and the second subset of the synchronized data;

determining, using at least the first subset of the synchronized data, that at least one of the plurality of feature points represents a moving object; and creating a map using one or more of the plurality of feature points, the one or more of the plurality of feature points not including the at least one of the plurality of feature points that represents the moving object.

10. The method of claim 9, wherein determining the plurality of feature points of the physical area using at least the first subset of the synchronized data and the second subset of the synchronized data comprises:

comparing the first subset of the synchronized data with the second subset of the synchronized data to determine whether the first subset of the synchronized data and the second subset indicate an erroneous movement signal; and based on determining that the first subset of the synchronized data and the second subset indicate an erroneous movement signal, detecting the plurality of feature points in one or more images captured by the camera and represented by the first subset of the synchronized data.

11. The method of claim 10, wherein detecting the plurality of feature points in the one or more images captured by the camera and represented by the first subset of the synchronized data comprises detecting the plurality of feature points in two or more images captured by the camera and represented by the first subset of the synchronized data.

12. The method of claim 10, wherein detecting the plurality of feature points in one or more images captured by the camera and represented by the first subset of the synchronized data comprises:

determining a sensor priority scheme for the two or more sensors;

determining, using the sensor priority scheme, that the camera has a higher priority than the other sensor; and selecting the first subset of the synchronized data in response to determining that the camera has a higher priority than the other sensor.

13. The method of claim 9, comprising:

receiving second data from the two or more sensors;

synchronizing the received second data from the two or more sensors so that the second data from the camera corresponds in time to the second data from a third sensor;

determining a third subset of the synchronized second data from the camera for a second period of time and a fourth subset of the synchronized second data from the third sensor for the second period of time;

comparing the third subset of the synchronized second data with the fourth subset of the synchronized second data to determine whether the third subset and the fourth subset indicate an erroneous movement signal;

based on determining that the third subset and the fourth subset indicate an erroneous movement signal, selecting, from the third subset and the fourth subset of the synchronized second data, third data for one of the sensors, the selection based on a sensor priority scheme for the sensors;

determining that the selected third data for one of the sensors indicate that the computer is not moving; and discarding the third subset and the fourth subset of the synchronized second data in response to determining that the selected third data for one of the sensors indicate that the computer is not moving.

14. The method of claim 13, wherein discarding the first subset and the second subset of the synchronized second data comprises determining not to update the map using the third subset and the fourth subset of the synchronized second data.

15. The method of claim 9, comprising determining navigation instructions using one or more of the plurality of feature points.

16. The method of claim 15, wherein determining the navigation instructions using one or more of the plurality of feature points comprises determining the navigation instructions using one or more of the at least one of the plurality of feature points that represents the moving object.

17. A non-transitory computer readable storage medium storing instructions executable by a computer and upon such execution cause the computer to perform operations comprising:

receiving data from two or more sensors included in the computer, the two or more sensors including a camera and another sensor;

synchronizing the received data from the two or more sensors so that the data from the camera corresponds in time to the data from the other sensor;

determining a first subset of the synchronized data from the camera for a period of time and a second subset of the synchronized data from the other sensor for the period of time, the first subset of the synchronized data and the second subset of the synchronized data each being representative of movement of the computer and the first subset of the synchronized data being representative of objects in a physical area surrounding a physical location of the computer;

determining a plurality of feature points of the physical area using at least the first subset of the synchronized data and the second subset of the synchronized data;

determining, using at least the first subset of the synchronized data, that at least one of the plurality of feature points represents a moving object; and creating a map using one or more of the plurality of feature points, the one or more of the plurality of feature points not including the at least one of the plurality of feature points that represents the moving object.

18. The computer readable storage medium of claim 17, wherein determining the plurality of feature points of the physical area using at least the first subset of the synchronized data and the second subset of the synchronized data comprises:

comparing the first subset of the synchronized data with the second subset of the synchronized data to determine whether the first subset of the synchronized data and the second subset indicate an erroneous movement signal; and based on determining that the first subset of the synchronized data and the second subset indicate an erroneous movement signal, detecting the plurality of feature points in one or more images captured by the camera and represented by the first subset of the synchronized data.

19. The computer readable storage medium of claim 18, wherein detecting the plurality of feature points in the one or more images captured by the camera and represented by the first subset of the synchronized data comprises detecting the plurality of feature points in two or more images captured by the camera and represented by the first subset of the synchronized data.

20. The computer readable storage medium of claim 18, wherein detecting the plurality of feature points in one or more images captured by the camera and represented by the first subset of the synchronized data comprises:

determining a sensor priority scheme for the two or more sensors;

determining, using the sensor priority scheme, that the camera has a higher priority than the other sensor; and selecting the first subset of the synchronized data in response to determining that the camera has a higher priority than the other sensor.

* * * * *

UNITED STATES PATENT AND TRADEMARK OFFICE
CERTIFICATE OF CORRECTION

PATENT NO. : 10,330,489 B1  
APPLICATION NO. : 15/585451  
DATED : June 25, 2019  
INVENTOR(S) : Andersson et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 213 days.

Signed and Sealed this  
Second Day of June, 2020

Andrei Iancu  
*Director of the United States Patent and Trademark Office*